United States Patent
Visser et al.

(10) Patent No.: US 11,937,887 B2
(45) Date of Patent: Mar. 26, 2024

(54) ULTRASOUND SYSTEM AND METHOD FOR TRACKING MOVEMENT OF AN OBJECT

(71) Applicant: KONINKLIJKE PHILIPS N.V., Eindhoven (NL)

(72) Inventors: Cornelis Gerardus Visser, Eindhoven (NL); Iris Verel, Eindhoven (NL); Raja Sekhar Bandaru, Eindhoven (NL); Jeire Steinbuch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 129 days.

(21) Appl. No.: 17/611,213

(22) PCT Filed: May 13, 2020

(86) PCT No.: PCT/EP2020/063276
§ 371 (c)(1),
(2) Date: Nov. 15, 2021

(87) PCT Pub. No.: WO2020/234070
PCT Pub. Date: Nov. 26, 2020

(65) Prior Publication Data
US 2022/0061932 A1  Mar. 3, 2022

(30) Foreign Application Priority Data

May 17, 2019 (EP) ..................................... 19175161
Dec. 4, 2019 (EP) ..................................... 19213547

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/4254* (2013.01); *A61B 8/54* (2013.01); *A61B 2034/2063* (2016.02)

(58) Field of Classification Search
CPC ..... A61B 34/20; A61B 8/0841; A61B 8/4254; A61B 8/54; A61B 2034/2063
See application file for complete search history.

(56) References Cited

U.S. PATENT DOCUMENTS 5,750,897 A * 5/1998 Kato .................... G03F 7/70833
  73/DIG. 1
6,733,458 B1   5/2004 Steins
(Continued)

FOREIGN PATENT DOCUMENTS

JP  2008113699 A  5/2008
WO  2018149671 A1  8/2018

OTHER PUBLICATIONS

International Search Report and Written Opinion of PCT/EP2020/063276, dated Sep. 9, 2020.

*Primary Examiner* — Serkan Akar
*Assistant Examiner* — Amal Aly Farag

(57) ABSTRACT

A system and method for tracking an object (14) received within a body (16) using ultrasound wherein shifts in position of an ultrasound probe (20) tracking the object (either deliberate or accidental) can be corrected for. The method comprises tracking a position of the object through the body using an ultrasound transducer unit, and sensing movement of the ultrasound transducer unit using a physically coupled motion sensor (26). From the movement of the ultrasound transducer unit, movement of its field of view (24) can be determined. Based on a tracked history of positions (28) of the object through the field of view, and on the tracked movement of the field of view relative to the (Continued)

body, a direction of motion of the object through the body can be derived.

18 Claims, 3 Drawing Sheets

(51) Int. Cl.
*A61B 8/08* (2006.01)
*A61B 8/12* (2006.01)
*A61B 8/14* (2006.01)
*A61B 10/02* (2006.01)
*A61B 17/34* (2006.01)
*A61B 34/10* (2016.01)
*A61B 90/00* (2016.01)
*G06T 7/20* (2017.01)
*G06T 7/246* (2017.01)

(56) References Cited

U.S. PATENT DOCUMENTS

| | | | |
|---|---|---|---|
| 2002/0143275 A1* | 10/2002 | Sarvazyan | A61B 5/036 600/587 |
| 2006/0182320 A1 | 8/2006 | Peszynski | |
| 2006/0270934 A1* | 11/2006 | Savord | G01S 15/8993 600/437 |
| 2010/0298704 A1 | 11/2010 | Pelissier | |
| 2015/0178886 A1 | 6/2015 | Pfister | |
| 2015/0201911 A1* | 7/2015 | Halmann | A61B 10/04 600/424 |
| 2016/0317119 A1* | 11/2016 | Tahmasebi Maraghoosh | A61B 8/467 |
| 2017/0095226 A1* | 4/2017 | Tanaka | A61B 8/4416 |
| 2017/0172539 A1 | 6/2017 | Vignon | |
| 2018/0168537 A1 | 6/2018 | Hsieh | |

* cited by examiner

ULTRASOUND SYSTEM AND METHOD FOR TRACKING MOVEMENT OF AN OBJECT

CROSS-REFERENCE TO PRIOR APPLICATIONS

This application is the U.S. National Phase application under 35 U.S.C. § 371 of International Application No. PCT/EP2020/063276, filed on May 13, 2020, which claims the benefit of European Patent Application Serial No. 19175161.9, filed May 17, 2019 and European Patent Application No. 19213547.3, filed on Dec. 4, 2019. These applications are hereby incorporated by reference herein.

FIELD OF THE INVENTION

The present invention relates to the field of ultrasound imaging, and more specifically to the field of tracking an object, such as a tool, received within a body, using ultrasound.

BACKGROUND OF THE INVENTION

Precise visualization of objects, e.g. medical tools such as needles or catheters, received within a body is often required, for instance for certain minimally invasive interventions. Real-time localization of an object with respect to imaged anatomy is also often used.

Ultrasound (US) imaging is one of the most popular imaging systems for tool guidance applications. Ultrasound imaging may be used to image tools such as needles, laparoscopes, stents, and radioactive seeds used for brachytherapy. For example, ultrasound imaging may be used for needle guidance in anesthesiology, tissue ablation or for biopsy guidance, since needles are used to take tissue samples, and to deliver medicine or electrical energy to the targeted tissue inside a patient's body. During these procedures, visualization of the needle and its tip is very important in order to minimize risk to the patient and improve health outcomes.

Various ultrasound systems are available in the market, which utilize some method for tracking the location of an object in the body of the patient. Such systems share the common attribute that each detected position of the object is digitally represented in the system, allowing display of the positions, and that the positions are updated periodically, typically in conjunction with active scanning, such that the real-time ultrasound image display can also show the detected location of the object being tracked.

Some systems offer a means of showing the path of the detected object in the image, either as a history (where the object came from), or future extrapolation (where it will go if moved in the same direction), or both. Generating such a projected path is typically by means of a method well understood in the art. One method is to include a mechanical fixture like a needle guide mounted on the ultrasound probe which simply constrains the object to follow a predetermined path, i.e., to physically constrain the path of the object with respect to the ultrasound probe as the object is inserted. Other means include locating the device by magnetic or electro-magnetic (EM) sensing of the location of the object with respect to similar sensing of the ultrasound probe position. In further examples, an ultrasound-based location sensor can be used to track the needle position. This sensor is coupled to the inserted part of the needle, and either detects US energy received from the US probe to determine a changing path distance, or reflects energy back to the probe, the probe then determining changing path distance based thereon.

Typically, 2D or 3D ultrasound guidance is used to visualize an object while a procedure is being conducted.

An example of an object that is tracked during an ultrasound procedure is a needle.

During needle biopsy and some interventional therapy, clinicians insert a needle into a subject, such as the body, to reach a target mass. For regional anesthesia, a needle is used to deliver anesthetic to the vicinity of a target nerve bundle in the body, typically in preparation for a surgical procedure. Usually ultrasound imaging is used for live monitoring of the needle insertion procedure. To perform a safe and successful insertion, it is necessary to locate the needle accurately in the guided ultrasound image.

A particular impediment with known ultrasound tracking procedures is that while the position of the object is continuously and accurately located in the displayed ultrasound image, the ultrasound probe itself may be rotated or translated with respect to the object, which leads to shifting of the imaging field of view (FOV) or imaging plane. This is hence effectively a shift of the co-ordinate system within which the object is being tracked. The shift of the field of view is largely indistinguishable from motion of the object itself in the medium being scanned, therefore leading to inaccuracy in the object position tracking.

An approach has been previously proposed to mitigate this problem. WO 2018/149671 proposes an approach wherein responsive to detected movement of the probe, calculation of the tracked object position is temporarily suppressed to prevent the shifting field of view leading to calculation inaccuracies.

However, this intermittent suppression of object tracking leads to reduced accuracy or precision in the detected positions.

While this is acceptable for some applications of object tracking, for others, more exact position knowledge is required. By way of example, for needle tip tracking (NTT) used for vascular access (VA), the needle typically has a larger bevel length compared to NTT when used for regional anesthesia (RA). This leads to a larger distance between the needle tip and the position of the ultrasound sensor on the needle, which results in a larger circle of possible tip positions (about the tracked ultrasound sensor position).

Another document U.S. Pat. No. 6,733,458 B1 discloses a diagnostic medical ultrasound system having an integrated invasive medical device guidance system. The guidance system obtains image slice geometry and other imaging parameters from the ultrasound system to optimize the guidance computations and visual representations of the invasive medical device and the imaged portion of the subject. Further, the ultrasound system obtains guidance data indicating the relative location, i.e. position and/or orientation of the invasive medical device relative to the transducer and imaging plane to optimize the imaging plane and ultrasound beam characteristics to automatically optimally image both the imaged portion of the subject and the invasive medical device.

Another document US 2018/0168537 A1 discloses a needle guide system including a puncture device, an ultrasound transducer, a first orientation detector, a second orientation detector, a proximity detector and a processor. The ultrasound transducer is configured to obtain an ultrasound image. The first orientation detector is disposed on the puncture device, and the second orientation detector is disposed on the ultrasound transducer. The proximity detector is disposed on at least one of the puncture device and the ultrasound transducer, configured to obtain a relative distance between the puncture device and the ultrasound transducer. The processor is configured to obtain a spatial relationship between the puncture device and the ultrasound transducer by using the first orientation detector, the second orientation detector, and the proximity detector, and predict a trajectory of the puncture device in the ultrasound image according to the spatial relationship.

Another document US 2010/0298704 A1 discloses an ultrasound system having an ultrasound transducer equipped with a position marker and a needle equipped with a position marker. The position markers allow the position and orientation of the transducer and needle to be determined. A display depicts an ultrasound image acquired via the transducer and a graphical element representative of a projection of the longitudinal axis of the needle onto a plane of the ultrasound image. The quality of the position and orientation information from the position markers is monitored, and when quality is below a quality threshold the display indicates this fact.

Another document US 2017/0172539 A1 relates to an ultrasound receive beamformer configured for one-way only beamforming of transmissive ultrasound using one-way delays. The receive beamforming in some embodiments is used to track, in real time, a catheter, needle or other surgical tool within an image of a region of interest. The tool can have embedded at its tip a small ultrasound transmitter or receiver for transmitting or receiving the transmissive ultrasound. Optionally, additional transducers are fixed along the tool to provide the orientation of the tool.

Another document WO 2018/149671 A1 discloses a method for determining a projected track of an object including measuring movement from frame to frame of a detected object point in a field of view by periodic comparison of positions, extrapolating a locus of periodically detected object points, and qualifying the locus by calculating and applying a threshold to the linearity in a sequence of positions and a threshold to consistency in strength. The method further produces the plurality of ultrasound images by including thereon a rendering of a plurality of lines as a path track indicator on one or more ultrasound images and displaying the projected track of the object when a user moves the tracked object a minimum distance in a region of interest of a subject. The method also includes utilizing a motion sensor with a probe to suppress calculation and display of the projected track.

An improved ultrasound object tracking approach, in which the problem of shifting ultrasound probe position is addressed, and wherein improved position detection accuracy is provided, would be of value.

SUMMARY OF THE INVENTION

The invention is defined by the claims.

According to examples in accordance with an aspect of the invention, there is provided an ultrasound system for tracking movement of an object received in a body, comprising an ultrasound transducer unit having an ultrasound imaging field of view, FOV;

a motion detector adapted to detect movement of the ultrasound transducer unit relative to the body; and a controller, operatively coupled with the ultrasound transducer unit and the motion detector, and configured to:

detect and track movement of said field of view over time relative to the body using data from the motion detector;

detect and track positions over time of the tracked object within the field of view;

generate an estimation of a direction of motion of the object through the body over time, based on a history of the detected object positions within the FOV over time, and taking into account the detected and tracked movement of said FOV relative to the body over time;

communicate with i) an ultrasound sensor incorporated in the object to be tracked, the ultrasound sensor for detecting ultrasound signals transmitted by the ultrasound transducer unit into the body or ii) an ultrasound emitter incorporated in the object to be tracked, the ultrasound emitter for emitting ultrasound signals within the body for detection by the ultrasound transducer unit, for use in tracking the object position;

track the position of a designated point (35) on the object, for example a tip of the object; and to determine a range or a span of possible current positions of said designated point of the object within the field of view, based on a known distance between said designated point and the respective i) ultrasound sensor, or ii) ultrasound emitter, incorporated in the object, and based on the tracked positions of the object.

Embodiments of the present invention are based on providing a further movement detector, such as an IMU (inertial measurement unit) or other motion sensor coupled to the ultrasound probe, and using this sensor for keeping reference between the ultrasound image plane the history of object positions.

The ultrasound transducer unit may be configured for acquiring 2D or 3D ultrasound data for example. Where 3D ultrasound imaging is used, object tracking may, by way of one example approach, comprise tracking a position of an object within one or more 2D imaging planes within the 3D field of view.

Embodiments of the invention facilitate improved accuracy in object tracking in two ways.

First, by additionally tracking movement of the ultrasound transducer unit (e.g. ultrasound probe) over time, and using this to determine movement of the field of view over time, the movement of the field of view can be factored into the estimation of the object movement, i.e. compensating or accounting for field of view shifts (in combination with detected movement of the object within the field of view). These two parameters together allow for overcoming shifts in the field of view, without compromising accuracy of the object movement tracking.

Secondly, embodiments of the present invention have the feature of deriving directional information for the object movement, rather than simply a current position of the object. As will be explained, this directional data provides a means to more accurately locate the object position within the body. The directional information of the object is derived from a tracked history of positions of the object over time during the procedure, in combination with the FOV movement data. From these data, an estimated resultant direction of motion of the object (or a trajectory of the object through the body) over time can be plotted and derived. Once a direction of the object is known, a much narrower range of possible positions of the object may be derived, and provided to a user. The directional information also has other potential uses as part of accurate object tracking.

Embodiments of the invention are thus able to provide more accurate or precise positional and directional information regarding the object without increasing the number of parts included in the tracked object itself. For instance, it is not necessary to include multiple different tracking sensors within the tracked object to improve tracking accuracy, which would increase the size of the object, potentially compromising or complication procedures being performed using the object.

The direction of movement of the object may in some circumstances change over time. The controller may therefore be adapted to derive an instantaneous direction of motion at each current moment or point and/or may determine a full motion path or trajectory of the object through the body over time.

The detecting and tracking positions over time of the tracked object within the field of view may be performed using ultrasound data generated by the ultrasound transducer unit.

For example, the detecting and tracking of movement of said field of view over time may be based on analysis of ultrasound data generated by the ultrasound transducer unit. In some examples for instance, image processing may be performed (for instance in real time), the image processing including an object detection procedure for detecting and tracking a position of the tracked object within generated ultrasound images of the field of view.

In further examples, detecting and tracking of positions over time of the tracked object within the field of view may be based on use of an additional ultrasound sensor coupled to the object being tracked, the sensor configured to detect transmitted ultrasound energy and communicate with the controller to facilitate tracking. This is explained in more detail below. In yet further examples, detecting and tracking of positions over time of the tracked object within the field of view may be based on use of an ultrasound emitter coupled to the object being tracked, the emitter being configured to emit ultrasound energy for detection by the ultrasound unit and communicate with the controller to facilitate tracking.

Estimation of the direction of motion of the object, while taking into account the movements in the field of view, may comprise performing one or more co-ordinate system transformations responsive to detected movement of the field of view. A co-ordinate system for the field of view relative to the body may be transformed in these processes to compensate or correct for the movement of the ultrasound transducer unit.

A major benefit of embodiments of this invention is that both in-plane and out-of-plane object movement can be tracked. In-plane refers to object tracking in which the object movement is parallel or substantially parallel with a 2D imaging plane scanned by the transducer unit. Out-of-plane object tracking refers to object tracking in which the object movement is non-parallel, for instance transverse or perpendicular to a 2D imaging plane scanned by the transducer unit. For out-of-plane tracking, typically the probe is swept or tilted to move the imaging plane to follow the tracked object through the body. Since any movement of the field of view (e.g. the imaging plane) is tracked and automatically accounted for in object position tracking, either of these tracking approaches (in-plane or out-of-plane) can be accommodated.

The ultrasound transducer unit may be an ultrasound probe, e.g. a handheld ultrasound imaging probe. The ultrasound transducer unit comprises one or more ultrasound transducers operable to transmit and receive ultrasound signals. The ultrasound transducer unit is preferably a 2D ultrasound unit.

The motion detector may be an accelerometer in examples. A gyroscope and/or magnetometer may additionally or alternatively by used. The body may in examples be assumed to be stationary relative to the ground, such that any movement detected by the accelerometer may be assumed to be movement of the ultrasound transducer unit relative to the body.

The controller may be further configured to generate guidance information for adjusting a positioning of the ultrasound transducer unit or the object.

The guidance information may be for guiding an operator in moving the object toward a target location, e.g. a target blood vessel for probing or puncturing the object, or for receiving the object. For instance the object may be a tool, e.g. an ultrasound-guided needle. The guidance information may be for guiding a user in aligning the object within the imaging field of view for improved visualization of the object.

The guidance information may by way of example be for guiding a user in adjusting (e.g. an initial) positioning of the ultrasound transducer unit so as to move a 2D imaging plane acquired by the transducer unit to coincide with a location of the object (i.e. so as to adjust a position of the 2D imaging plane so as to contain the object being tracked). Without this guidance, a user may not know whether the object (e.g. needle tip) is initially in front of or behind the imaging plane position. Therefore, it may be more difficult to attain a correct imaging plane position for capturing the tracked object.

The controller may be further configured to determine a trajectory or movement path of the object through the body over time, for example, based on a derived direction of motion at different time points.

The object to be tracked may include an ultrasound sensor for communicating with the controller to facilitate tracking of the object position over time. The ultrasound sensor includes an ultrasound receiver for receiving ultrasound signals from the ultrasound transducer unit. It may be operatively coupled with the controller. Based at least partly on a sensor output from the ultrasound sensor, the controller may determine a location of the ultrasound within the body over time. For example, the controller may compare timings of ultrasound signal transmission (by the transducer unit) and signal receipt at the ultrasound sensor, and use this to facilitate estimation of location of the object over time.

Alternatively or additionally to including an ultrasound sensor, the object to be tracked may include an ultrasound emitter for communicating with the controller to facilitate tracking of the object position over time. The ultrasound emitter emits ultrasound signals for detection by the ultrasound transducer unit. In other words, the emitted signals may have a frequency that is detectable by the ultrasound transducer unit. The emitter may be operatively coupled with the controller, which may for example provide electrical signals for generating the emitted ultrasound signals. The ultrasound emitter may thus act as an ultrasound beacon, the ultrasound signals emitted from which may be detected by the ultrasound transducer unit when the ultrasound emitter is disposed within its field of view. Based at least partly on the ultrasound signals detected by the ultrasound transducer unit, for example based on the time of flight and a beam in which the ultrasound signals are detected selected from the beams that form the field of view of the ultrasound transducer unit, the controller may determine a location of the ultrasound emitter within the body over time. For example, the controller may compare timings of ultrasound signal emission by the ultrasound emitter and signal receipt at the ultrasound transducer unit, and use this to facilitate estimation of location of the object over time. In other examples the ultrasound signals may be processed in the same manner as ultrasound imaging signals detected by the ultrasound transducer unit, i.e. using its imaging pipeline, and thus the detected ultrasound signals from the ultrasound emitter appear as a bright spot in the ultrasound image.

Accordingly, the controller of the system may be adapted to communicate with an ultrasound sensor incorporated in the object to be tracked, the ultrasound sensor for detecting ultrasound signals transmitted by the ultrasound transducer unit into the body. The ultrasound sensor is for use in tracking the object position. It includes an ultrasound signal receiver. It includes for example one or more ultrasound transducers.

Alternatively or additionally the controller of the system may be adapted to communicate with an ultrasound emitter incorporated in the object to be tracked, the ultrasound emitter for emitting ultrasound signals within the body for detection by the ultrasound transducer unit. The ultrasound emitter is for use in tracking the object position. It includes an ultrasound signal detector. It includes for example one or more ultrasound transducers.

Processing of signals received at the ultrasound sensor may be performed locally at the ultrasound sensor or by the controller in different examples.

The controller may be adapted to track the position of a designated point on the object, for example a tip of the object, for example the tip of a needle.

Where an ultrasound sensor/emitter is used to facilitate object tracking, the location of the tracked point on the object may be different to the location of the ultrasound sensor/emitter within the object. This can lead to some uncertainty in the exact position of the designated point, since usually only the location of the ultrasound sensor/emitter is directly detectable.

The controller may be adapted to determine a range or span of possible current positions of said designated point of the object within the field of view, based on a known distance between said designated point and the ultrasound sensor/emitter incorporated in the object, and based on the tracked positions of the object. This may be a circle of possible positions.

More preferably, this is an arc of possible positions within the field of view, and is determined based in part on the determined direction of motion of the object. By taking into account the derived direction of motion of the object, the range of possible positions of the tracked point can be reduced (narrowed) to just an arc, or just a sector of a circle or a smaller circle.

The controller is configured to generate a visual representation of said determined range or span of possible positions for output to a display unit for displaying to a user. The controller may render on a screen a graphical representation of the object historical trajectory (e.g. with a line) and show a circle, arc or circle sector indicating the possible position of the designated tracked point on the object (e.g. the tip).

The display unit may be an external unit, not part of the provided ultrasound system, or it may be part of the ultrasound system.

The controller may be configured for instance to generate a control signal for controlling a display device to display a visual representation of the direction of movement and/or a derived trajectory of the object.

In examples, the estimating the direction of motion of the object may include fitting a straight line through the history of object positions.

In advantageous applications, the object may be a needle, and the system is configured to track the motion of a tip of the needle.

In certain embodiments, the provided ultrasound system may include the object to be tracked. The object may incorporate i) an ultrasound sensor for detecting ultrasound signals transmitted by the ultrasound probe into the body, or ii) ultrasound emitter for emitting ultrasound signals within the body for detection by the ultrasound probe. This ultrasound sensor/emitter may be adapted to communicate with the controller of the system (for use in tracking the object position).

Examples in accordance with a further aspect of the invention provide an ultrasound processing method for use in tracking movement of an object received in a body, the method utilizing an ultrasound transducer unit having an imaging field of view, and the method comprising:

detecting movement of the ultrasound transducer unit over time relative to the body and detecting and tracking movement of the field of view relative to the body based on said detected movement;

detecting and tracking positions over time of the tracked object within the field of view; and generating an estimation of a direction of motion of the object through the body over time, based on a history of the detected object positions within the FOV over time, and based on the detected and tracked movement of said FOV relative to the body over time.

The method may further comprise determining a range or span of possible current positions of said designated point of the object within the field of view, based on a known distance between said designated point and i) an ultrasound sensor incorporated in the object and configured to detect ultrasound signals transmitted into the body by the ultrasound transducer unit, or ii) an ultrasound emitter incorporated in the object and configured to emit ultrasound signals within the body for detection by the ultrasound transducer unit, and based on the tracked positions of the object.

The method preferably is a computer implemented method. In such case one or more preferably all of the steps are performed and/or controlled by a computer. The computer may thus have a controller configured to control or perform the method steps.

Examples in accordance with a further aspect of the invention provide a computer program product comprising instructions which, when the program is executed by a computer, cause the computer to carry out the steps of any of the example methods described herein.

The computer program product may be storable or downloadable from a network or may be executed from such network as for example with cloud based operation, or may be stored on a computer readable medium such as magnetic hard disk, optical disk, of solid state memory. The computer program product may be stored in a memory on the ultrasound system.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
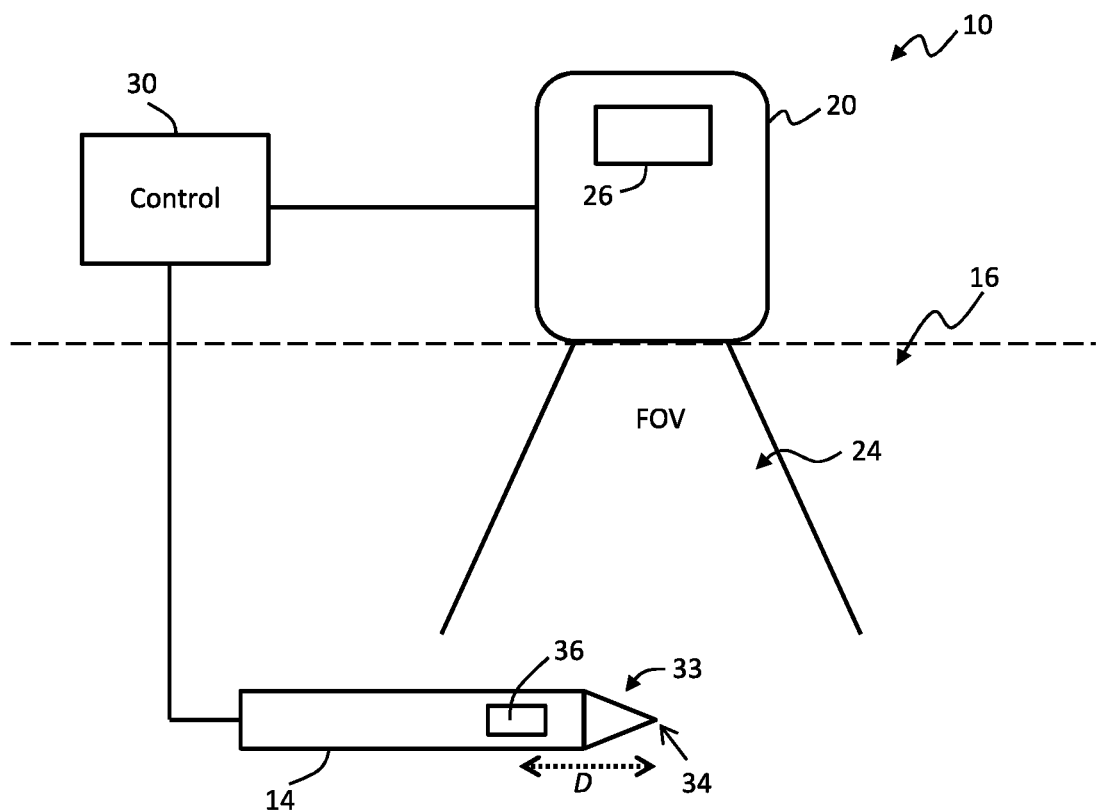
FIG. 1 shows an example ultrasound system according to one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system and method for tracking an object received within a body using ultrasound wherein shifts in position of an ultrasound probe tracking the object (either deliberate or accidental) can be corrected for. The method comprises tracking a position of the object through the body using an ultrasound transducer unit, and sensing movement of the ultrasound transducer unit using a physically coupled movement sensor. From the movement of the ultrasound transducer unit, movement of its field of view can be determined. Based on a tracked history of positions of the object through the field of view, and on tracked movement of the field of view relative to the body, a direction of motion of the object through the body can be derived.

In certain embodiments, this can be used to more accurately estimate a location of a specific point on the object, e.g. a tip of the object.

Embodiments of the invention find advantageous application for tracking a position of a medical tool inserted into a body. One example is an ultrasound guided needle. Needle tip tracking (NTT) is a well-known field, and is used to track the tip of a needle inserted into a subject's body for example for administering regional anesthesia or for vascular access (VA). Vascular access refers to a rapid, direct method of introducing or removing devices or chemicals to or from the bloodstream.

As discussed above, a major challenge with current approaches is that the 2D ultrasound probe tracking the object can move relative to the body. When the 2D probe moves, the ultrasound image plane moves accordingly and the tracked history of object positions lose their reference with respect to the body. Accuracy in detecting position within the body is therefore compromised.

Furthermore, an additional challenge is accommodating object tracking in cases wherein the object trajectory is not perfectly aligned with the ultrasound probe imaging field of view. Typically, the field of view is a 2D plane. If the movement of the object is not aligned parallel with this plane, the object will move in and out of the field of view as it is moved through the body. This makes tracking its position within the field of view difficult without shifting the field of view, which leads to inaccuracy as noted above.

A related challenge is accommodating out-of-plane (OOP) movement of the object. By this is meant procedures in which the object is moved in a direction non-parallel (e.g. perpendicular or transverse) to the 2D imaging plane of the ultrasound probe. In OOP procedures the ultrasound probe is often moved to follow the object during insertion. Again, since the object is not moving within a fixed field of view, it is difficult to determine the needle movement direction relative to the body.

Embodiments of the present invention provide a motion detector incorporated in the ultrasound transducer unit to detect and monitor movement of the transducer unit (relative to the body). This allows tracking movement of the field of view. Embodiments are based on estimating a direction of motion of the object through the body taking into account both the tracked object positions through the FOV and the tracked movements of the FOV itself. Thus, challenges associated with position shifts of the probe (discussed above) can be ameliorated.

FIG. 1 schematically illustrates an example ultrasound system according to one or more embodiments. The ultrasound system 10 is for tracking movement of an object 14 received in a body 16. For example, the body is the body of a subject or patient undergoing a minor intervention requiring insertion of a medical tool to the body. The object may be a medical tool, for example a needle for performing local delivery of anesthesia or for vascular access.

The system comprises an ultrasound transducer unit 20. The ultrasound transducer unit may be an ultrasound probe, for example a handheld ultrasound probe. It includes one or more ultrasound transducers. It preferably includes a transducer array. The transducer unit is preferably operable to perform 2D ultrasound imaging across a 2D ultrasound imaging plane.

The ultrasound transducer unit 20 has an imaging field of view (FOV) 24. The imaging field of view may be three-dimensional in some examples, for example it may be approximately pyramidal in shape (or frusto-pyramidal), or conical (or frustro-conical) for example. However, the shape is not essential to the invention and any other shape is possible. In use, the transducer unit is positioned at the surface of the body 16 being probed (e.g. at the skin of the subject's body), above the location in the body in which the object 14 is to be received. Ultrasound signals are transmitted into the body by the transducer unit 20 across the field of view 24.

The ultrasound transducer unit may be configured to acquire 3D ultrasound data representative of the whole, or a 3D volume portion, of the field of view. Alternatively, the transducer unit may acquire one or more 2D imaging planes. The particular imaging plane acquired may vary over time, for example the depth at which the imaging plane is acquired in the body may vary to enable imaging at multiple depths. These represent examples only, and the skilled person will be aware of many different approaches to performing both 2D and 3D ultrasound imaging.

A motion detector or sensor 26 is further provided, adapted to detect movement of the ultrasound transducer unit 20 relative to the body 16. In the present example, a motion detector is incorporated within the ultrasound transducer unit. It may include for instance an accelerometer, a gyroscope and/or a magnetometer.

A controller 30 is further provided, operatively coupled with the ultrasound transducer unit 20 and the motion detector 26 of the transducer unit.

The controller 30 is configured to perform processing steps for deriving an estimate of a location and/or direction of motion of (at least a portion of) the object 14. These steps will now be outlined.

The controller 30 is configured to detect and track movement of the field of view 24 over time relative to the body 16 using data from the motion detector 26. This will be described in greater detail below. In brief, sensor output signals from the motion sensor are converted by the controller into corresponding resultant movements of the FOV.

The controller 30 is further configured to detect and track positions over time of the tracked object 14 within the field of view 24, using ultrasound data generated by the ultrasound transducer unit 20.

The controller 30 is configured to generate an estimation of a direction of motion of the object 14 through the body 16 over time, based on a history of the detected object positions 26 within the FOV 24 over time, and based on the detected and tracked movement of said FOV relative to the body over time.

Detecting and tracking the object positions within the field of view 24 over time can be done in different ways. In advantageous examples, the object 14 to be tracked includes an ultrasound sensor/emitter 36 for communicating with the controller 30 to facilitate tracking of the object position over time. This example is illustrated in FIG. 1.

The ultrasound sensor/emitter 36 includes an ultrasound receiver/transmitter, comprising one or more ultrasound transducers, for receiving/emitting ultrasound signals from the ultrasound transducer unit/for detection by the ultrasound transducer unit. It may be operatively coupled with the controller 30. Based at least partly on i) a sensor output from the ultrasound sensor, or ii) an ultrasound signal detected by the ultrasound transducer unit in response to an ultrasound signal emitted by the ultrasound emitter, the controller may determine a location of the ultrasound sensor within the body over time. For example, the controller may compare timings of ultrasound signal transmission (by the transducer unit/ultrasound emitter) and signal receipt at the ultrasound sensor/transducer unit, and use this to facilitate estimation of location of the object over time.

The controller 30 in this example is operatively coupled with at least the ultrasound sensor 36 of the object 14 being tracked. The ultrasound sensor detects ultrasound signals transmitted into the body 16 by the ultrasound transducer unit. Based on for instance timing of detection of the signals, an estimated position of the ultrasound sensor 36 can be determined by the controller 30. This position may then be taken as representative of the position of the object 14 within the body. Likewise when an ultrasound emitter is used the ultrasound emitter emits ultrasound signals within the body, and an estimated position of the ultrasound emitter 36 may be determined by the controller 30 based on for instance the time of detection of the ultrasound signals and a beam of the ultrasound transducer unit in which the ultrasound signals are detected.

In certain examples, signals may be transmitted sequentially from multiple different transducers or subsets of transducers, located at different positions across an output surface of the transducer unit 20. A location of the ultrasound sensor 36 inside the FOV 24 may then be determined with greater certainty, based on analyzing timings of receipt (or time of flight) of each of the transmitted signals at the ultrasound sensor 36. A triangulation process may be used in some examples, using signals transmitted (e.g. sequentially) from each of the plurality of transducer units and received at the ultrasound sensor.

The ultrasound sensor itself may in some examples be configured to transmit ultrasound signals, for receipt at each of the plurality of ultrasound transducer units. Analyzing time of flight of each of these signals to the respective ultrasound transducer may enable a position of the tracked object to be determined more precisely, for example with triangulation or any other method.

Although in the example of FIG. 1, the tracked object includes an ultrasound sensor/emitter 36 to facilitate tracking, this is not essential. Tracking of the object 14 may be performed based only on analysis of image data or images received or derived from the ultrasound transducer unit. For instance, shape-matching may be used to identify the location of the object within each image frame generated using the ultrasound data, and the location tracked over a series of frames, to thereby track the location over time.

In certain examples, the controller 30 may be adapted to track the position of a designated point 34 on the object 14, for example a tip of the object. This is illustrated in FIG. 1.

By way of example, the designated point 34 may be a tip of the object, for example the tip of a needle. This is illustrated in FIG. 1 where the object shown is a needle having a beveled distal end 33 ending in a tip, and a designated point 34 is shown corresponding to the tip of the needle. In needle tip tracking (NTT), the position of the needle tip is determined and tracked.

Figure 5:
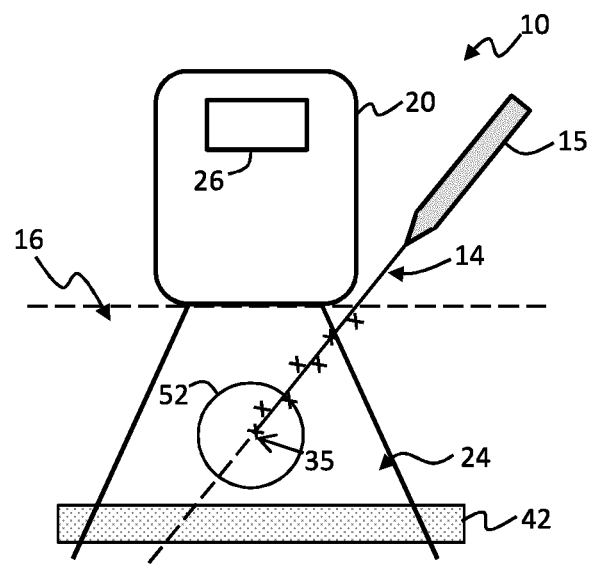
FIG. 5 illustrates deriving a circle of possible positions for a designated point of an object.

The designated point 34 may typically be at a different location on the object 14 to that of the ultrasound sensor/emitter 36. In FIG. 1 for example, the tip is shown at a location a distance D from the ultrasound sensor/emitter 36. Thus, tracking the tip position in this case requires extrapolating the tip position from the directly derived positions of the ultrasound sensor/emitter. This means that, ordinarily, knowledge of the position of this point is limited to a circle 52 of possible positions, centered on the ultrasound sensor/emitter 36, and with radius equal to a distance, D, between the ultrasound sensor/emitter and the designated point. Thus is illustrated in FIG. 5, and will be discussed in more detail later. The further derived direction of motion information discussed above can be used to narrow the range of possible locations of the designated point. This will also be discussed in greater detail later.

The invention involves estimating a direction of motion of the object through the body over time.

Deriving the direction of motion of the object takes into account both the history of object positions within the transducer unit FOV 24, and the detected movements of the field of view.

This can be done with different specific approaches. At a high level, the controller 30 is configured to perform registration of the field of view 24 with the history of object positions.

This may comprise detecting and tracking shifts in position of the field of view 24 (relative to the body 16), and performing transformations of a co-ordinate system of the field of view to compensate or correct for the movements. The detected object positions over time are recorded relative to this field of view co-ordinate system. By suitably transforming the co-ordinate system to correct for any movements of the field of view, correct registration between the recorded object positions and the field of view is maintained. As a result, the recorded object positions remain in registration with the body co-ordinate system, such that an accurate history of positions of the object within the body is achieved.

The shifts in position of the imaging field of view 24 are detected using the motion sensor 26 incorporated in the ultrasound transducer unit 20. Movement detected by this sensor directly corresponds to movements in the imaging field of view.

The motion sensor 26 can take different forms. By way of example, it may comprise an accelerometer, a gyroscope, a magnetometer or a combination of two or more of these. Other examples are also possible, such as for instance image based movement detection (detecting movement shifts based on analysis of ultrasound images derived from the probe ultrasound data). Any suitable movement detection means may be used.

A pre-stored algorithm may be applied to convert the raw sensor output signals from the motion sensor(s) into corresponding resultant spatial shifts in the field of view. A lookup table might alternatively be used for this task in simple examples.

The additional movement information from the motion sensor 26 coupled to the ultrasound probe 20 enables a direction of movement of the object 14 through the body 16 to be established with greater accuracy and certainty. This in turn enables a path or trajectory of the object through the body to be established with greater accuracy.

A series of local or instantaneous directions of motion of the object 14 may in some examples be derived, corresponding to different time points (e.g. to accommodate changes in direction over time). At each time point, an instantaneous direction of motion may be derived based on a local/regional subset of the history of object positions.

Additionally or alternatively, a single average or overall direction of motion may be derived based on the complete history of positions of the object 14. This may be recurrently updated, e.g. at each new time point.

A trajectory of the object 14 through the body 16 may be derived based on the history of tracked positions of the object. A single straight line trajectory, corresponding to an average trajectory through the body may be derived. The directionality of this line corresponds to an average or overall direction of motion of the object. Alternatively, a path of the object's historical movement through the body may be derived, which may be curved or incorporate differently directioned sections. Such a path of the object's movement may incorporate multiple local or instantaneous directions of motion corresponding to different time points.

Deriving a direction of motion or a trajectory of the object 14 may be performed based on fitting a trajectory line through the history of positions of the object (or at least a subset of them). The controller 30 may apply a pre-stored algorithm to perform this task. Preferably, the algorithm applied by the controller to derive the trajectory of the object through the body may include features or steps to exclude or manage outlier position points.

Figure 2:
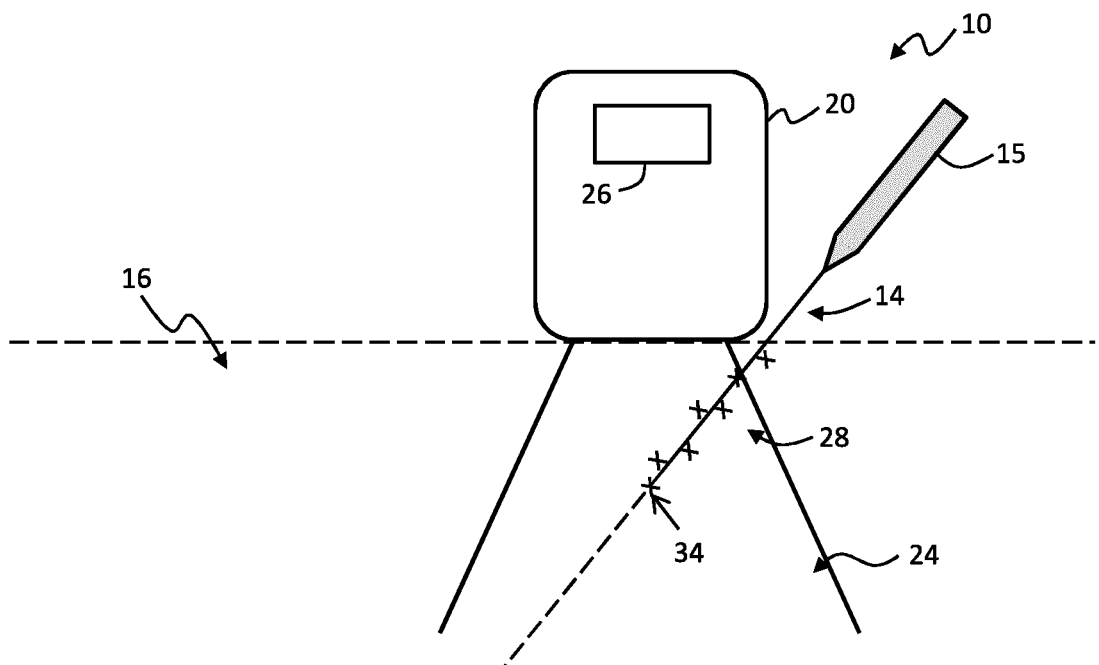
FIG. 2 shows an example ultrasound system in use.

FIG. 2 schematically illustrates an example ultrasound system 10 in use. For ease of illustration, the controller 30 is not shown in FIG. 2.

The object 14 to be tracked in this example is a needle. The needle is manipulated by an operator via a proximal handle 15. In use, the ultrasound transducer unit 20 is placed at the subject's skin above the location for insertion of the needle, and the needle is inserted by the operator into the subject's body 16 from the skin surface. As it is moved into the body, the needle follows (in this illustration) an approximately linear trajectory through the body. The controller 30 tracks the moving location of the needle (e.g. of an ultrasound sensor/emitter included at a near-distal portion of the needle), using ultrasound data from the ultrasound transducer unit 20 and optionally also data from an ultrasound sensor/emitter incorporated in the needle (if an ultrasound sensor/emitter is provided). The controller records a history of positions 28 of the object 14 within the imaging field of view 24 of the ultrasound transducer unit. The history of object positions 28 is represented by the crosses in FIG. 2. The controller may track the position of the tip 34 of the needle through the body.

The controller 30 determines a trajectory line of the of the needle 14 through the body 16, as illustrated in FIG. 2 based on the history positions 28, and using the movement data from the motion sensor 26 to compensate for any movement of the ultrasound probe 20. The controller 30 may plot an extrapolated future trajectory path of the object 14 through the body (indicated by the dotted line in FIG. 2).

As noted above, the ultrasound system 10 may advantageously be applied to both in-plane object 14 insertion procedures and out-of-plane object insertion procedures. In-plane refers to a case in which the direction of motion of the object is aligned, or parallel with, the imaging plane 24 (i.e. the plane of the 2D imaging field of view 24) of the ultrasound transducer unit 20. Out-of-plane means a case in which the movement of the object is oblique to or non-parallel with the imaging plane.

Figure 3:
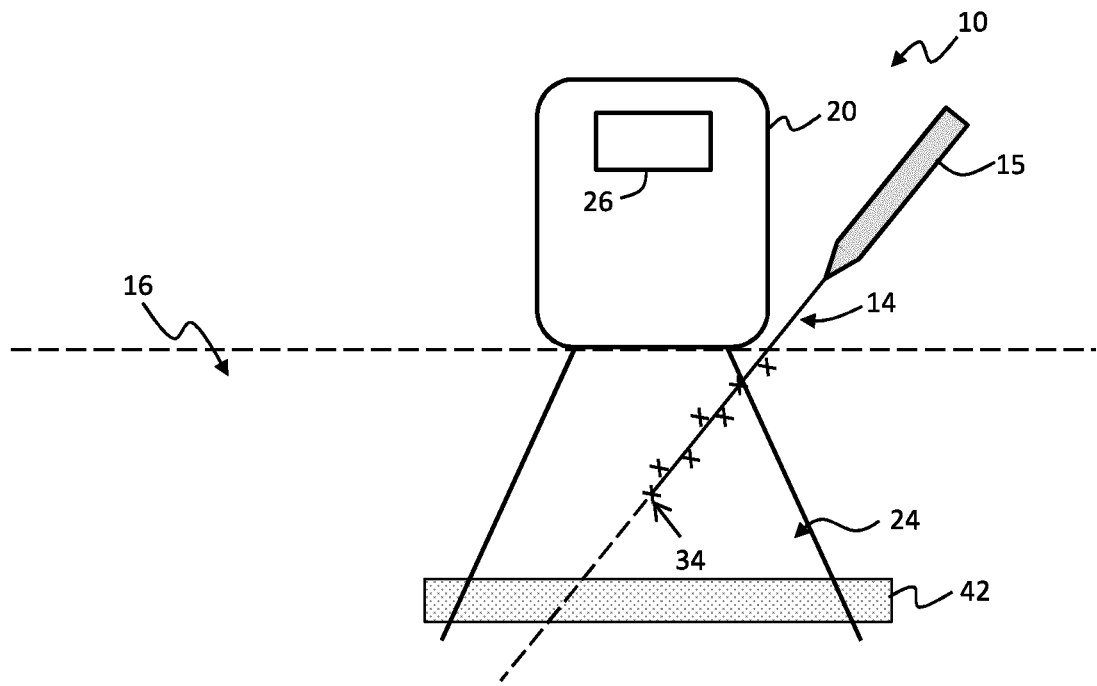
FIGS. 3 and 4 show an example ultrasound system in use during an in-plane and out-of-plane movement procedure respectively.

FIG. 3 schematically illustrates use of an example system 10 in tracking a needle through a body 14 during an in-plane procedure. The needle is being guided toward a target blood vessel 42. The trajectory of the needle through the body in this example is parallel (in plane with) the field of view 24 of the ultrasound transducer unit 20.

Figure 4:
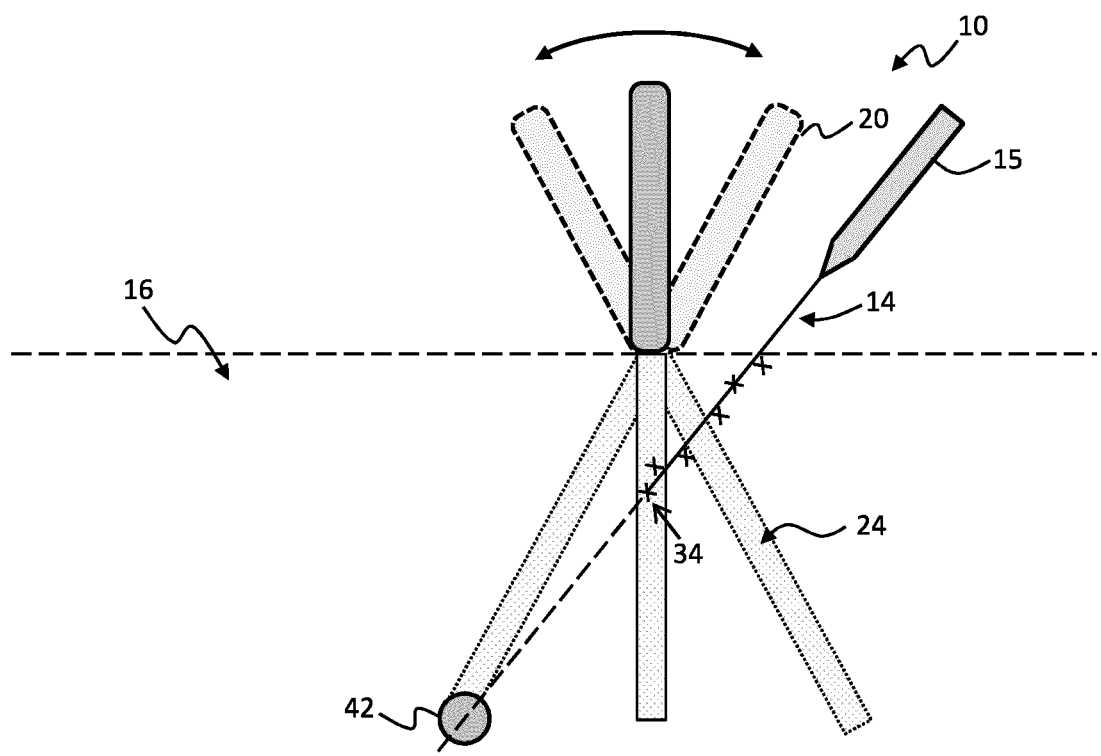

FIG. 4 schematically illustrates use of an example system 10 in tracking a needle through a body 14 during an out-of-plane procedure. The needle is again being guided toward a target blood vessel 42. The ultrasound transducer unit is in the form of a hand-operated ultrasound probe 20. In this example, the field of view (the imaging plane) 24 of the ultrasound probe 20 is transverse (e.g. approximately perpendicular) the trajectory of the object 14 into the body 16 toward the target vessel 42 (i.e. is extending into the page, from the perspective of FIG. 4). In this case, the ultrasound probe 20 is tilted relative to the body skin surface as the needle is inserted so as to move the imaging plane 24 to follow the distal end of the needle 14.

The tilting of the probe 20 and the resultant shift in the field of view 24 is detected and tracked as discussed above, and the direction of motion of the needle through the body accurately determined with this movement taken into account.

The results of this processing performed by the controller 30 can be used in different ways to provide useful information to the user.

The derived direction or directions of motion of the object 14 through the body may be visualized to the user, for example on a display unit arranged in communication with the controller 30. Any derived trajectory or path of the object through the body over time may be visualized. This may be visualized for instance with a displayed line overlaid on a rendered representation of the body.

The derived direction(s) of motion of the object over time may be used to derive further information or estimations.

For example, it may in some examples be used to derive a more accurate estimate of the location of a particular designated point 35 on the object 14. For example, this point may be at a different location on the object to that of the ultrasound sensor/emitter 36 used for tracking the position of the object within the ultrasound field of view 24. This means that, ordinarily, knowledge of the position of this point is limited to a circle of possible positions, centered on the ultrasound sensor/emitter 36, and with radius equal to a distance, D, between the ultrasound sensor/emitter 36 and the designated point 35.

By way of example, the designated point 35 may be a tip of the object, for example the tip of a needle. This is illustrated in FIG. 5, where the object shown is a needle, and a designated point 35 is shown corresponding to the tip of the needle. In needle tip tracking (NTT), the position of the needle tip is determined and tracked. The circle 52 of possible positions of the needle tip is shown. This circle of possible positions may be rendered and displayed to a user on an associated display panel in certain embodiments, to assist the user in guiding the needle through the body 16.

For certain procedures, in particular for vascular access (VA) using a needle, the bevel of the needle (the beveled distal section of the needle) is longer than is used for certain other procedures, such as for instance local anesthesia delivery. This longer bevel means the ultrasound sensor/emitter-needle tip distance, D, is longer, and the uncertainty in the needle tip position greater (the radius of the circle 52 is larger).

Knowledge of direction of motion of the needle 14 enables a position of the designated point 35 on the object to be estimated with greater certainty.

For example, in the case of the needle tip 34 being the designated point 35 which is tracked, knowing the needle movement direction means it can be assumed that the needle tip lies at a point forward of, and parallel with, the derived linear trajectory line of the object 14 through the body 16. The trajectory line may be simply extrapolated forward by a distance equal to the known distance, D, between the ultrasound sensor/emitter 36 and the needle tip 34, 35. This allows knowledge of the needle tip position to be narrowed to just an arc 53 of possible positions, or just a sector of the previously possible circle 52 of positions.

Figure 6:
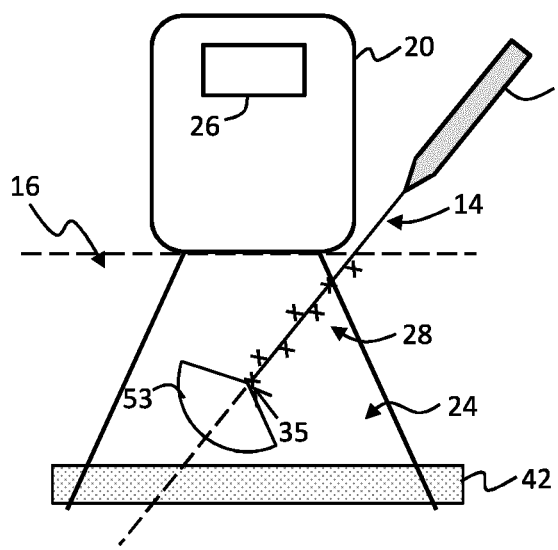
FIGS. 6 and 7 illustrate reduction of the range of possible positions to an arc of positions, using an embodiment of the invention.
Figure 7:
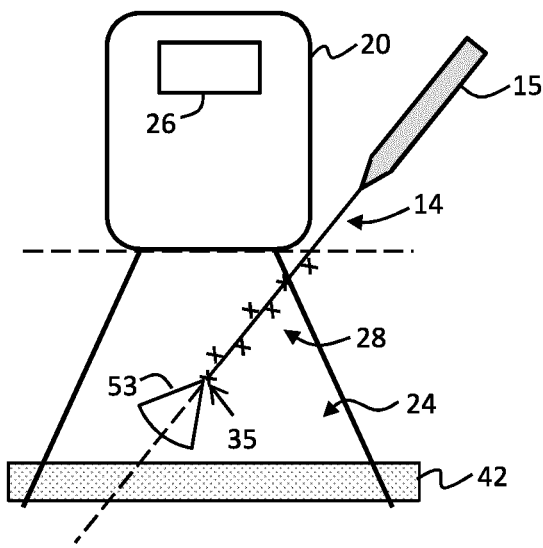

This is illustrated schematically in FIG. 6 and FIG. 7, which show reduction of the circle 52 of possible positions of the needle tip to just a sector 53 or arc of the circle. The sector becomes narrower with increasing quality of the line fit through the history 28 of the object positions. The quality of the line fit is in part a function of the number of position points 28 forming the history of object positions. Thus, the size of the sector 53 may be reduced by detecting the object position at a greater frequency, i.e. at more frequent time intervals as the object is moved through the body 16.

The results of the processing performed by the controller 30 may be used according to one or more embodiments to generate guidance information for the user. This may include information for guiding an operator in moving the object toward a target location, e.g. a needle toward a target blood vessel to which access is desired.

Guidance information may be generated for guiding a user to better align the imaging plane or field of view 24 with the direction of object motion. This may be guidance for adjusting a position or orientation of the ultrasound transducer unit 20 or for adjusting the movement trajectory of the object 14 being moved through the body 14.

Although the various example systems above have been described in terms of application to needle tip tracking, this is for illustration only. Each described example, and the invention more generally, may be applied to a wide range of different specific applications. Embodiments may be applied for tracking any object which is to be inserted into a body. The body may be a human or animal body, or may be an inanimate body. The object may be a medical tool, or may be for instance an implantable element or device, or may be a tool inserted into a non-organic body. For example, the system may track movement of an inspection tool through a portion of a building, such a wall or floor or ceiling cavity, or through pipework for instance.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An ultrasound system for tracking movement of an object in a medical procedure, the ultrasound system comprising: an ultrasound probe having an imaging field of view (FOV); a motion detector configured to detect movement of the ultrasound probe relative to a body and generate data on the movement of the FOV relative to the body; and a controller, operatively coupled with the ultrasound probe and the motion detector, the controller configured to: detect the movement of the FOV relative to the body using the data generated by the motion detector, communicate with at least one of i) an ultrasound sensor incorporated in the object and configured to detect ultrasound signals transmitted by the ultrasound probe and ii) an ultrasound emitter incorporated in the object and configured to emit ultrasound signals for detection by the ultrasound probe, detect positions of the object within the FOV based on the communication with the at least one of the ultrasound sensor and the ultrasound emitter, record, over time, a history of the detected positions of the object within the FOV, generate an estimation of a direction of motion of the object based on the recorded history of the detected positions of the object within the FOV and based on the detected movement of the FOV relative to the body, and determine a range of possible current positions of a designated point of on the object within the FOV based on a known distance between the designated point and i) the ultrasound sensor or ii) the ultrasound emitter incorporated in the object and based on the detected positions of the object, wherein the determined range of possible current positions is a circle centered on i) the ultrasound sensor or ii) the ultrasound emitter with a radius equal to a distance between the designated point and i) the ultrasound sensor or ii) the ultrasound emitter, and narrow the range of possible current positions by selection of an arc of the circle of the possible current positions based on the generated estimation of the direction of motion of the object.

2. The ultrasound system as claimed in claim 1, wherein the controller is further configured to generate guidance information for adjusting a positioning of the ultrasound probe or the object.

3. The ultrasound system as claimed in claim 1, wherein the controller is further configured to determine a trajectory or movement path of the object through the body based on the generated estimation of the direction of motion of the object.

4. The ultrasound system as claimed in claim 1, wherein the ultrasound probe is configured to generate ultrasound data from at least one of the ultrasound signals transmitted to the ultrasound sensor and the ultrasound signals emitted by the ultrasound emitter, and the controller is configured to detect the positions of the object within the FOV using ultrasound data generated by the ultrasound probe.

5. The ultrasound system as claimed in claim 1, wherein the controller is further configured to narrow the range of possible current positions of the designated point of the object within the FOV based on the generated estimation of the direction of motion of the object.

6. The ultrasound system as claimed in claim 1, wherein the controller is configured to generate a visual representation of the determined range of possible current positions for output to a display for displaying to a user.

7. The ultrasound system as claimed in claim 6, wherein the controller is configured to estimate the direction of motion of the object based on fitting a straight line through the recorded history of the detected positions of the object.

8. The ultrasound system as claimed in claim 1, further comprising the object with the at least one of i) the ultrasound sensor and ii) the ultrasound emitter incorporated in the object.

9. A non-transitory computer-readable storage medium storing a computer program comprising instructions which, when executed by a processor, cause the processor to: detect movement of an ultrasound probe relative to a body, the ultrasound probe having a FOV; detect the FOV relative to the body based on the detected movement of the ultrasound probe; communicate with at least one of i) an ultrasound sensor incorporated in an object and configured to detect ultrasound signals transmitted by the ultrasound probe and ii) an ultrasound emitter incorporated in the object and configured to emit ultrasound signals for detection by the ultrasound transducer probe; detect positions of the object within the FOV based on the communication with the at least one of i) the ultrasound sensor or ii) the ultrasound emitter; record, over time, a history of the detected positions of the object within the FOV, generate an estimation of a direction of motion of the object through the body, based on the recorded history of the detected positions of the object within the FOV and based on the detected movement of said FOV relative to the body; and determine a range of possible current positions of a designated point on the object within the FOV based on a known distance between the designated point and i) the ultrasound sensor or ii) the ultrasound emitter incorporated in the object and based on the detected positions of the object, wherein the determined range of possible current positions is a circle centered on i) the ultrasound sensor or ii) the ultrasound emitter with a radius equal to a distance between the designated point and i) the ultrasound sensor or ii) the ultrasound emitter, and narrow the range of possible current positions by selection of an arc of the circle of the possible current positions based on the generated estimation of the direction of motion of the object.

10. The non-transitory computer-readable storage medium as claimed in claim 9, wherein the instructions, when executed by the processor, further cause the processor to: determine a trajectory or movement path of the object through the body based on the generated estimation of the direction of motion of the object.

11. The non-transitory computer-readable storage medium as claimed in claim 9, wherein the instructions, when executed by the processor, further cause the processor to: narrow the range of possible current positions of the designated point of the object within the field of view based on the generated estimation of the direction of motion of the object.

12. A computer implemented ultrasound processing method for use in tracking movement of an object in a medical procedure, the method comprising: detecting movement of an ultrasound probe having an imaging field of view relative to a body and detecting movement of the FOV relative to the body based on the detected movement of the ultrasound probe; communicating with at least one of i) an ultrasound sensor incorporated in the object and configured to detect ultrasound signals transmitted by the ultrasound probe and ii) an ultrasound emitter incorporated in the object and configured to emit ultrasound signals for detection by the ultrasound probe; detecting positions of the object within the FOV based on the communication with the at least one of i) the ultrasound sensor and ii) the ultrasound emitter; recording, over time, a history of the detected positions of the object within the FOV, generating an estimation of a direction of motion of the object through the body, based on the recorded history of the detected positions of the object within the FOV and based on the detected movement of the FOV relative to the body; and determining a range of possible current positions of a designated point on the object within the FOV based on a known distance between the designated point and i) the ultrasound sensor or ii) the ultrasound emitter incorporated in the object and based on the detected positions of the object, wherein the determined range of possible current positions is a circle centered on i) the ultrasound sensor or ii) the ultrasound emitter with a radius equal to a distance between the designated point and i) the ultrasound sensor or ii) the ultrasound emitter, and narrow the range of possible current positions by selection of an arc of the circle of the possible current positions based on the generated estimation of the direction of motion of the object.

13. The method as claimed in claim 12, further comprising determining a trajectory or movement path of the object through the body based on the generated estimation of the direction of motion of the object.

14. The method as claimed in claim 12, further comprising narrowing the range of possible current positions of the designated point of the object within the FOV based on the generated estimation of the direction of motion of the object.

15. The non-transitory computer-readable storage medium as claimed in claim 9, wherein the instructions, when executed by the processor, further cause the processor to:
   determine the range of possible current positions as a circle centered on i) the ultrasound sensor or ii) the ultrasound emitter with a radius equal to a distance between the designated point and i) the ultrasound sensor or ii) the ultrasound emitter, and
   narrow the range of possible current positions by selection of an arc of the circle of the possible current positions based on the generated estimation of the direction of motion of the object.

16. The non-transitory computer-readable storage medium as claimed in claim 9, wherein the instructions, when executed by the processor, further cause the processor to:
   generate a visual representation of the range of possible current positions for output to a display for displaying to a user.

17. The non-transitory computer-readable storage medium as claimed in claim 9, wherein the instructions, when executed by the processor, further cause the processor to:
   estimate the direction of motion of the object based on fitting a straight line through the recorded history of the detected positions of the object.

18. The method as claimed in claim 12, further comprising:
   generating a visual representation of the range of possible current positions and displaying the visual representation to a user.

\* \* \* \* \*